US005908635A

United States Patent [19]
Thierry

[11] Patent Number: 5,908,635
[45] Date of Patent: Jun. 1, 1999

[54] METHOD FOR THE LIPOSOMAL DELIVERY OF NUCLEIC ACIDS

[75] Inventor: Alain Thierry, Bethesda, Md.

[73] Assignee: The United States of America as represented by the Department of Health and Human Services, Washington, D.C.

[21] Appl. No.: 08/286,730

[22] Filed: Aug. 5, 1994

[51] Int. Cl.⁶ .................................................. A61K 9/127
[52] U.S. Cl. .......................................... 424/450; 424/400
[58] Field of Search ............................................. 424/450

[56] References Cited

U.S. PATENT DOCUMENTS

| | | | |
|---|---|---|---|
| 5,171,678 | 12/1992 | Behr | 435/172.3 |
| 5,279,833 | 1/1994 | Rose | 424/450 |
| 5,283,185 | 2/1994 | Epand | 435/172.3 |

FOREIGN PATENT DOCUMENTS

| | | |
|---|---|---|
| 93/05162 | 3/1993 | WIPO . |
| 94/05624 | 3/1994 | WIPO . |
| 95/21259 | 8/1995 | WIPO . |

OTHER PUBLICATIONS

Gao Xinag et al., "Cationic Liposomes and Polymers for Gene Transfer", Journal of Liposomes Research, vol. 3, No. 1, 1993, pp. 17–30.
B. Clary et al., "Adeno–Associated Virus Plasmid: Cationic Liposomal–Mediated Gene Transfer Results in Significant Cytokine Gene Expression in Human Tumor Cells Following Lethal Irradiation," Surgical Forum, vol. 44, 1994, pp. 530–533.
F. Barthel et al., "Laboratory Methods—Gene Transfer Optimization with Lipospermine–Coated DNA," DNA and Cell Biology, vol. 12, No. 6, 1993, pp. 553–560.
N. Zhu et al., "Systematic Gene Expression After Intravenous DNA Delivery into Adult Mice," Science, vol. 261, Jul. 9, 1993, pp. 209–211.
K. Yoshimura et al., "Adenovirus–Medicated Augmentation of Cell Transfection With Unmodified Plasmid Vectors," The Journal of Biological Chemistry, No. 4 Issue, Feb. 3, 1993, pp. 2300–2303.
H. Farhood et al., "Effect of Cationic Cholesterol Derivatives on Gene Transfer and Protein Kinase C Activity," Biochimica et Biphysica Acta, (1992) pp. 239–246.
R. J. Cristiano et al., "Hepatic Gene Therapy: Adenovirus Enhancement of Receptor–Mediated Gene Delivery and Expression in Primary Hepatocytes," Genetics, vol. 90, Mar. 1993, pp. 2122–2126.
X. Gao et al., "A Novel Cationic Liposome Reagent For Efficient Transfection Of Mammalian Cells," Biochemical and Biophysical Research Communications, vol. 179, No. 1, Aug. 30, 1991, pp. 280–285.
E. G. Nabel et al., "Site–Specific Gene Expressing In Vivo By Direct Gene Transfer Into the Arterial Wall," Science, vol. 249, Sep. 14, 1990, pp. 1285–1288.
J.P. Behr et al., "Efficient Gene Transfer Into Mammalian Primary Endocrine Cells With Lipopolyamine–Coated DNA," Proc. Nat'l Acad. Sci., vol. 86, Sep. 1989, pp. 6982–6986.

(List continued on next page.)

Primary Examiner—Thurman K. Page
Attorney, Agent, or Firm—Morgan & Finnegan, L.L.P.

[57] ABSTRACT

The present invention is directed to a liposomal preparation which is based on specific lipid components. The liposomal compounds are also combined with nucleic acids, forming nucleic acid-liposomal compounds. These compounds are useful in drug delivery, where specific therapeutic nucleic acids are used in the liposomes. The specific lipid components of the present invention provide a highly efficient and stable delivery system for nucleic acids. Consequently, the liposomal preparations are suitable for use in gene therapy.

22 Claims, 5 Drawing Sheets

OTHER PUBLICATIONS

P. L. Felgner et al., "Lipofection: A Highly Efficient, Lipid–Mediated DNA–Transfection Procedure," Proc. Natl. Acad. Sci., vol. 84, Nov. 1987, pp. 7413–7417.

C. Yen Wang et al., "pH–Sensitive Immunoliposomes Mediate Target–Cell–Specific Delivery and Controlled Expression Of A Foreign Gene In Mouse," Proc. Natl. Acad. Sci., vol. 84, Nov. 1987, pp. 7851–7855.

P. Soriano et al., "Targeted And Nontargeted Liposomes for In Vivo Transfer To Rat Liver Cells Of A Plasmid Containing The Plasmid I Gene," Proc. Natl. Acad. Sci, vol. 80, Dec. 1983, pp. 7128–7131.

METHOD FOR THE LIPOSOMAL DELIVERY OF NUCLEIC ACIDS

FIELD OF THE INVENTION

The present invention is directed to a liposomal preparation which is based on a composition of nucleic acids or analogues and specific lipids which form liposomes. It is also an object of the present invention to provide a method for preparing a liposomal nucleic acid composition which is simple and very efficient.

BACKGROUND OF THE INVENTION

As advances continue to be made in the molecular biology of inherited or acquired diseases, modulation or modification of the genetic program of living cells is looked upon with growing interest as a new therapeutic approach. Two different strategies have emerged: Gene therapy and oligonucleotide-based therapeutics. To be successful these two approaches must be mediated by an efficient "in vivo" transfer of the nucleic acid material to the target cells and there is a need to provide an efficient and safe delivery system of nucleic materials.

Gene therapy involves the transfer of normal, functional genetic material into cells to correct an abnormality due to a defective or deficient gene product. Typically, the genetic material to be transferred should at least contain the gene to be transferred together with a promoter to control the expression of the new gene. In general, two gene transfer strategies are considered: Viral (retrovirus or adenovirus) vectors and synthetic gene-transfer vectors.

Viral agents have been demonstrated to be highly efficient vectors for the transfection of somatic cells. Retroviruses in particular have received a great deal of attention because they not only enter cells efficiently, but also provide a mechanism for stable integration into the host genome through the provirus. However, clinical use of retroviral vector is hampered by safety issues. A first concern is the possibility of generating an infectious wild type virus following a recombination event. A second concern is the consequences of the random integration of the viral sequence into the genome of the target cell which may lead to tumorigenic event. In addition, as retroviruses would only complete their life cycle in dividing cells, a retroviral vector would be inefficient in targeting cells which are not dividing. DNA viruses such as adenoviruses are potential gene carriers but this strategy is limited in the size of the foreign DNA adenoviruses can carry and because of the restricted host range. However, the advantage of adenoviruses over retroviral vectors is their ability to infect post-mitotic cells.

Synthetic gene-transfer vectors have been subject to intense investigation since this strategy appears to be clinically safe. Potential methods of gene delivery that could be employed include DNA/protein complexes (1) or liposomes (2–7). The genetic material to be delivered to target cells by these methods are plasmids. Plasmids are recombinant DNA which are circular forms of double stranded DNA. They are constructed so that they have, at the minimum, a promoter and the gene coding for the protein of interest. Plasmids can be expressed in the nucleus of the transfected cells in a transient manner. In rare events, the plasmids may be integrated or partly integrated in the cell host genome and might therefore be stably expressed. Episomal plasmid vectors are plasmids able to replicate in the nucleus of the transfected cells and may therefore be expressed in a total growing cell population. Plasmids may have a promising potential considering the fact that they may be applied in combination with a synthetic vector as carrier and that gene therapy by this means may be safe, durable, and used as drug-like therapy.

Plasmid preparation is simple, quick, safe, and inexpensive representing important advantages over retroviral vector strategy. The successful use of this genetic tool for "in vivo" approaches to gene therapy will rely on the development of an efficient cell delivery system.

Liposomes have been shown to be efficient vehicles for many in vitro and in vivo applications. Liposome encapsulated DNA have been used in vitro (3,5) and in vivo (2,4,6,7) for the expression of a given gene through the use of plasmid vectors. The term "liposomes" describes a closed structure composed of lipid bilayers surrounding an internal aqueous space. Liposomes may be used to package DNA for delivery to cells, even in the case of plasmids of large size which could potentially be maintained in a soluble form that would allow direct application to in vivo systems by a simple intravenous injection. Formation of complexes of DNA with cationic liposomes has recently been the focus of research of many laboratories. In particular, lipofectin (Gibco BRL, Gaithersburg, Md.) has been successfully used for the transfection of various cell lines in vitro (3) and for systemic gene expression after intravenous delivery into adult mice (6).

Lipofectin is formed with the cationic lipid DOTMA, N[1-(2,3-dioleyloxy) propyl]-N,N,N-trimethyl-ammonium chloride, and DOPE, dioleylphosphatidyl ethanolamine at a 1:1 molar ratio. The liposomes prepared with this formulation spontaneously interact with DNA through the electrostatic interaction of the negative charges of the nucleic acids and the positive charges at the surface of the cationic liposomes. This DNA/liposomal complex fuses with tissue culture cells and facilitates the delivery of functional DNA into the cells (3). New cationic liposomes have been developed: Lipofectamine (Gibco BRL), composed of DOSPA, 2,3-dioleyloxy-N[2(sperminecarboxamido)ethyl]-N,N-dimethyl-1-propanaminium trifluoracetate and DOPE at a 1:1 molar ratio. Lipofectace (GIBCO BRL) composed of DDAB, dimethyidioctadecylammonium chloride and DOPE at a 1:1 molar ratio. DOTAP (Boehringer Mannheim, Ind.) 1-2-dioleoyloxy-3 (trimethyl ammonia) propane.

Behr et al. (9,10) have recently reported the use of a lipopolyamine (DOGS, Spermine-5-carboxy-glycinediotadecylamide) to transfer DNA to cultured cells. Lipopolyamines are synthesized from a natural polyamine spermine chemically linked to a lipid. For example, DOGS is made from spermine and dioctadecylamidoglycine (9). DOGS spontaneously condence DNA on a cationic lipid layer and result in the formation of nucleolipidic particles. This lipospermine-coated DNA shows high transfection efficiency (10).

It is an object of the present invention to provide an efficient and safe delivery system for nucleic acid materials.

SUMMARY OF THE INVENTION

The present invention relates to a nucleic acid-liposome preparation, useful in delivery of nucleic acid-based materials to cells. The present invention further relates to a method of preparing the nucleic acid-liposome preparations. In addition, the present invention relates to the administration of the nucleic acid-liposome preparations to cells. The invention further relates to administration of the nucleic acid liposome preparations to patients as a therapeutic agent.

The liposome compositions of the present invention provide highly efficient delivery of nucleic acids to cells. Liposome vesicles are prepared from a mixture of a cationic lipopolyamine and a neutral lipid. Nucleic acids are associated with the liposomes in two ways: (1)complex formation between the cationic liposome vesicle and negatively charged nucleic acid or (2) partial encapsulation and partial complex formation in and with the cationic liposome vesicle. A preferred embodiment of the present invention uses a spermine-5-carboxy-glycinedioctadecylamide (referred to herein as "DOGS") as the cationic lipopolyamine and dioleylphosphatidyl ethanolamine (referred to herein as "DOPE") as the neutral lipid.

Another embodiment of the present invention is directed to a combination of a DOGS/DOPE liposome preparation (referred to herein as "DLS-liposomes") anchored through hydrophobic interactions with an adenovirus particle. Since adenoviruses enter cells via receptor-mediated endocytosis, the combination of adenovirus particles and the DLS-liposomes produces an enhanced transduction efficiency.

One embodiment of the present invention is directed to a liposomal preparation which is based on a composition of nucleic acids or analogues and DOGS containing liposomes. The liposomes of the present invention efficaciously deliver nucleic acids into the cytoplasmic compartment of human cells. Use of such liposomal vehicles, and use of plasmid DNA as a carrier of a gene of interest, make possible high expression of such gene in cells or in a patient.

The present invention also encompasses a method of preparing such a composition. The presence of neutral lipid, such as DOPE or phosphatidylethanolamine in combination with a lipopolyamine such as DOGS makes possible the formation of liposomes after hydration, whereas use of lipopolyamine alone merely leads to the formation of lipid particles.

The liposomal preparations are further embodied in the present invention as a method for drug delivery suitable for use in gene therapy. Therefore the present invention is further directed to a method of treating a subject with a suitable formulation of nucleic acid-liposomes in order to deliver specific nucleic acids to target cells of the subject. Such a method of treating subjects provides effective delivery of oligonucleotides or gene-expressing plasmids into cells. Therefore, such a method of drug delivery is useful for the transport of nucleic acid based therapeutics.

The present invention provides a pharmaceutical liposomal formulation for the delivery of nucleic acids useful systemic administration and provides long-term expression of a given gene in dividing cells.

DETAILED DESCRIPTION OF THE INVENTION

Figure 1:
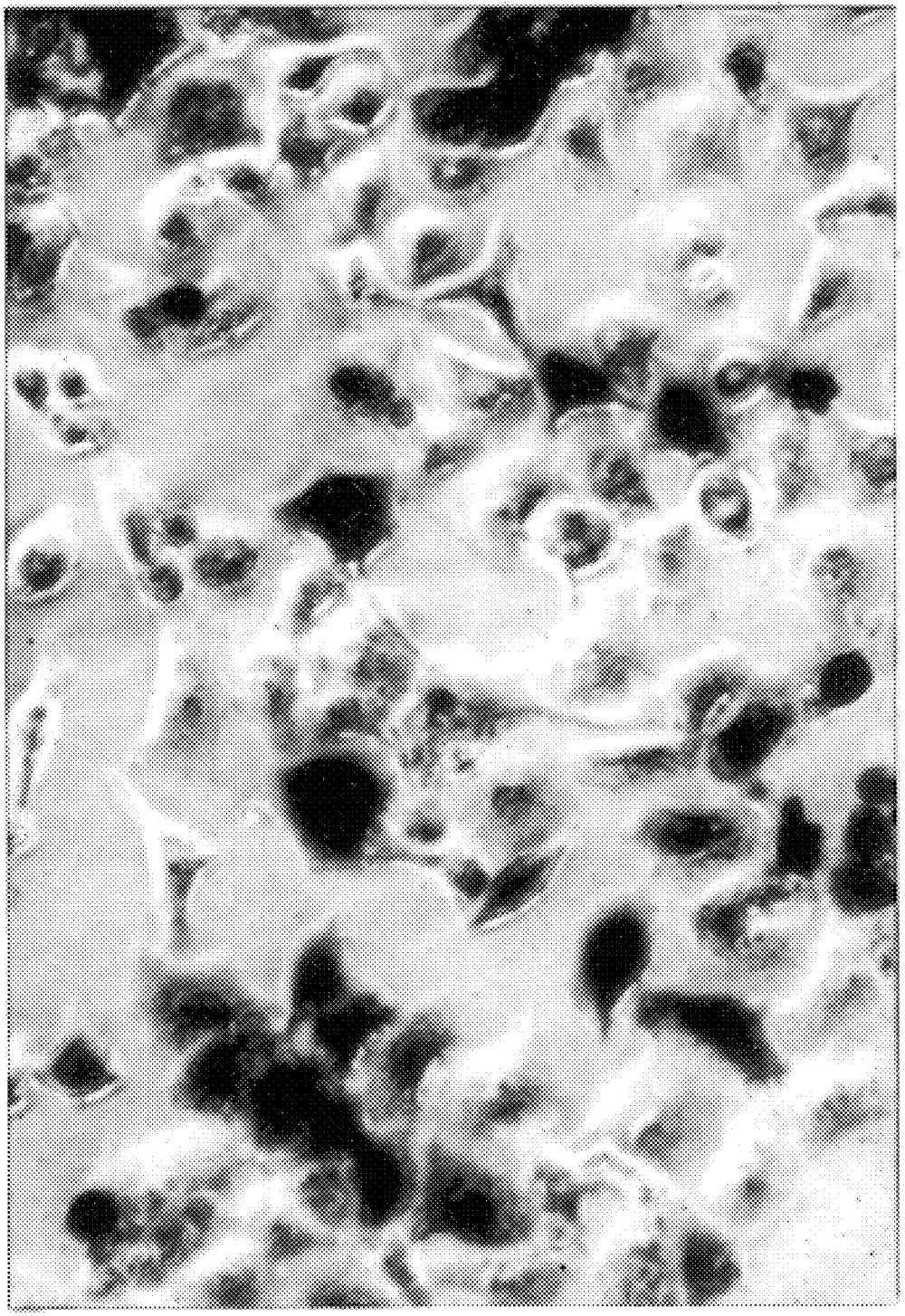
FIG. 1: β-Galactosidase expression in HeLa cells transfected with DOGS/DOPE liposomes (referred to herein as "DLS" liposomes).

The present invention relates to the discovery that nucleic acids may be associated with liposomes of a specific composition in a very effective manner. The liposome-associated nucleic acids may then be injected into a mammalian host to effectively express a given gene through the use of plasmid DNA, or to inhibit expression of a cellular gene through the use of antisense oligonucleotides. The efficiency of a liposome-mediated nucleic acid drug delivery system is directly dependent upon the liposome composition and its resulting association with cellular membranes.

Nucleic acids-based therapeutics may be of a broad use in therapy of a wide variety of diseases and disorders, such as, inherited or acquired genetic disease or viral infections.

The present invention may utilize one or more nucleic acids in conjunction with the liposomal carrier.

The term "nucleic acids" means any double strand or single strand deoxyribonucleic acid (DNA) or ribonucleic acid (RNA) of variable length. Nucleic acid analogs such as phosphorothioates, phosphoramidates, phosphonates analogs may be associated to the liposome composition in accordance with this invention. In one embodiment of the present invention, modified phosphorothioate oligonucleotides (alternatively referred to as "oligo(dN)") are used and demonstrate increased nuclease protection and increased cellular transport.

The liposomes of the present invention are prepared by drying a lipid mixture containing a lipopolyamine and then by hydrating the subsequent dry lipid film. Two methods of associating nucleic acids with liposomes are described in this invention. The first method comprises hydrating a dried lipid film by introducing an aqueous solution, and completely dispersing it by strongly homogenizing the mixture with a vortex, magnetic stirrer and/or sonication. Subsequent liposomes are mixed with a nucleic acid solution allowing complex formation between positive charges of the lipopolyamine-containing liposomes and the negative charges of the nucleic acids. The second method comprises hydrating the dried lipid film using a low and defined (5–10 μl/μg lipids) volume of aqueous solution containing concentrated nucleic acids. Dispersion is completed by strongly homogenizing the mixture using a vortex or magnetic stirrer. Nucleic acids are partly encapsulated in the liposomes during the formation and also are partly complexed through electrostatic interaction between the nucleic acid and the cationic liposomes.

The lipid mixture of the present invention must contain a lipopolyamine compound. Lipopolyamine, such as DOGS, condenses plasmid DNA and coats it with a cationic layer following simple mixing. Other lipopolyamines useful in the present invention include polyamines, spermidine and spermine. In order to form stable liposomes, the lipopolyamine is added to phosphatidylethanolamine (PE) or a derivative of PE such as DOPE (dioleoyl-phosphatidylethanolamine). For optimal transfection efficiency a DOGS/DOPE molar ratio of 0.5:1 is used. However, liposomes may be formed using a 0.1 to 5 molar ratio and showing significant nucleic acids delivery.

Such liposomes are mainly endocytosed by the cell and are consequently concentrated in intra-cytoplasmic vesicles. These endocytic vesicles release liposome content depending on the membrane fusogenic property of the liposomes and the nature of the liposome content. As drug therapy principally relies on the drug's ability to access the biological target, cytoplasmic delivery of nucleic acids transported through liposomes is critical. Enhancement of cytoplasmic delivery of liposome-associated compounds may be achieved using PE and especially the derivative DOPE in the liposome's composition.

Nucleic acids delivered using the carrier system of the present invention are efficiently released from endocytic vesicles and as a result a high cytoplasmic and nuclear distribution of nucleic acids is achieved.

The presence of DOPE or PE in combination with a lipopolyamine such as DOGS makes possible the formation of liposomes after hydration, whereas use of lipopolyamine only leads to the formation of lipid particles. Formation of phospholipidic bilayer membrane (liposomes) may allow for a enhanced blood circulation, stability and effectiveness of transduction. In addition, the liposomal membrane facilitates anchorage to its surface of other substituents, which can increase gene transfer and allow cell targeting, such as viral particles, virus fusogenic peptides or antibodies.

Liposomal delivery in accordance with the present invention may be used for increasing recombinant retrovirus infection. Retrovirus entry into cells is mediated via ligand-receptor recognition, and consequently their uptake is very low in certain cells which do not present those receptors. Associating a retrovirus or other recombinant virus to be used for gene therapy to liposomes may enhance penetration and/or expression of the viral agents.

The liposomal delivery system of the present invention makes possible high transduction efficiency in numerous cells such as human adenocarcinoma, HeLa, murine carcinoma, NIH3T3, human embryonic kidney 293, human leukemia MOLT-3 cell lines, and primary cultures of human macrophages and human vascular endothelial cells.

The two methods of forming the liposomes of the present invention lead to liposome-complexed and liposome-encapsulated nucleic acids, respectively. Liposome-encapsulated nucleic acids have been shown to be more efficient in transducing cells in cell cultures. However, the ability to sonicate the lipid vesicles in the liposome-complexed nucleic acids allow for more homogenized and smaller liposome particles, and consequently for the ability to circulate for longer periods in blood following systemic injection.

The liposomal composition of the present invention has shown to be stable in a biological environment, demonstrating that nucleic acids associated with the liposomal carrier are completely protected from enzymatic attack such as nucleases, and that stability in circulating blood after administration may be achieved.

The liposomal composition of the present invention may be systematically administered into patients parenterally in order to achieve gene therapy or oligonucleotide delivery. Moreover, this technique may be used for "ex vivo" gene therapy where tissue or cells are removed from patients, then treated and finally reimplanted in the patient.

Many diseases can be treated via the drug delivery system of the present invention. Diseases such as diabetes, atherosclerosis, and chemotherapy-induced multi-drug resistance can be treated using the present drug delivery system. One particular condition which can be treated via the system of the present invention relates to HIV and HIV-related diseases, such as anemia, leukopenia and thrombocytopenia. These clinical conditions are significantly related to a decrease or disappearance of hematopoietic progenitor cells in bone marrow of HIV-1 patients. Transfection of bone marrow stem cells, bone marrow stroma cells and embryonic stem with gene coding for immuno-restoring compounds might enhance the differentiation and proliferation capacity of such cells.

This delivery system can be useful for correcting the ion transport defect in cystic fibrosis patients by inserting the human CFTR (cystic fibrosis transmembrane conductance regulator) gene. Oral administration such as nebulization could particularly suitable. In addition, DLS-liposomes can be used for the inhibition of tumor cells by administering in tumor cells a gene coding for a molecule inhibiting tumorigenesis such as antisense oligonucleotides directed to angiogenic factors. Intra-lesional or intravenous administration appear suitable for this case.

The DLS-liposomes containing the nucleic acid drug can be administered by intravenous, intramuscular, intraperitoneal, subcutaneous intra-lesional and oral means.

A proposed daily dosage of active compound for the treatment of man is 0.5 mg DNA/kg to 4 mg DNA/kg, which may be conveniently administered in one or two doses. The precise dose employed will of course depend on the age and conditions of the patient and on the route of administration. Thus a suitable dose for administration by inhalation is 0.5 mg DNA/kg to 2 mg DNA/kg, for oral administration is 2 mg DNA/kg to 5 mg DNA/kg, for parenteral administration is 2 mg DNA/kg to 4 mg DNA/kg.

The compound of the invention may be formulated for parenteral administration by bolus injection or continuous infusion. Formulation for injection may be presented in unit dosage form in ampoules, or in multi-dose containers with an added preservative. The compositions may take such forms as suspension, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile pyrogen-free water, before use.

The compounds according to the invention may be formulated for administration in any convenient way. The invention therefore includes within its scope pharmaceutical compositions comprising at least one liposomal compound formulated for use in human or veterinary medicine. Such compositions may be presented for use with physiologically acceptable carriers or excipients, optionally with supplementary medicinal agents. Conventional carriers can also be used with the present invention.

For oral administration, the pharmaceutical composition may take the form of, for example, tablets, capsules, powders, solutions, syrups or suspensions prepared by conventional means with acceptable excipients.

The following examples serve to illustrate further the present invention and are not to be construed as limiting its scope in any way.

EXAMPLE 1

Preparation of a DOGS/DOPE-Containing Liposome Composition of the Invention

Liposomes are formed by mixing 1 mg DOGS and 1 mg DOPE (0.5:1 molar ratio). After thorough stirring, the mixture is evaporated to dryness in a round bottomed borosilicate tube using a rotary evaporator. The subsequent dried lipid film is resuspended in a low volume of ethanol (10 to 40 pl/mg lipid). Formation of liposomes is carried out by adding an excess of distillated water (at least 200 µl/mg lipid). After homogenization by slight vortexing, the mixture is incubated for at least 15 min. If needed, the resulting suspension may be sonicated in a fixed temperature bath at 25 C for 15 min.

EXAMPLE 2

Preparation of a DOGS/DOPE Liposome-Nucleic Acids Complex Composition

Complex formation of nucleic acids to the liposome bilayer membrane is achieved by simply mixing the preformed DOGS/DOPE liposomes (DLS-liposomes) to a solution of nucleic acids. In an Eppendorf tube, DLS-liposomes are mixed in a 150 mM NaCl solution to nucleic acids at a concentration of 12.5 µg total lipids (liposomes)/µg nucleic acid for double strand DNA, and a concentration of 6 µg liposomes/1 µg nucleic acid for oligonucleotides. The mixture is slightly mixed and incubated for at least 30 min at room temperature. Complex formation is very effective and nearly complete since at least 80% of nucleic acids were assimilated into the liposomes.

EXAMPLE 3

Preparation of DOGS/DOPE Liposome-Encapsulated Nucleic Acids Composition

Liposomes were formed by mixing 1 mg DOGS and 1 mg DOPE (0.5:1, molar ratio). After thorough stirring, the mixture is evaporated to dryness in a round bottomed borosilicate tube using a rotary evaporator. The subsequent dried lipid film is resuspended in a minimal volume (7 µl/mg lipid) of water solution containing nucleic acids (1400 µg/ml). Formation of liposomes is carried out by thorough stirring. The subsequent liposome preparation may be diluted in 150 mM NaCl. Entrapment and/or assimilation of nucleic acid by the liposomes is very efficient and nearly complete since at least 80% of nucleic acids are assimilated by the liposomes.

EXAMPLE 4

In Vitro Gene Transfection

Gene transfection efficacy was ascertained in vitro using reporter genes such as genes coding for p-galactosidase or luciferase. Two plasmid constructs containing the CMV (Clonetech) and RSV (Promega) promoters were used as genetic vectors for the β-galactosidase and luciferase genes, respectively. These plasmid vectors were delivered to the human carcinoma HeLa cells via the liposome carrier system in accordance with this invention.

One microgram liposomal DNA was added to the medium of a HeLa cell culture at a 50–70% confluency (500,000–700,000 cells/ml culture medium/7 $cm^2$ culture plate surface area). Cells were incubated at 37° C. with the liposomal DNA for at least 4 hr. Determination of gene expression was carried out for both types of plasmids following an incubation of 2–3 days at 37° C.

β-galactosidase activity was observed using a staining procedure after cell fixation on the culture plate using a conventional method. Cells expressing the β-galactosidase were readily identified by their intense blue staining. As shown in FIG. 1, more than 60% of the HeLa cells treated by DOGS/DOPE liposome-associated DNA, actively expressed β-galactosidase.

Luciferase activity was detected in HeLa cells using a standard method (Promega, Madison, Wis.). Luciferase gene containing plasmid was used for a comparative study of the transduction efficiency of the liposomal delivery in accordance with this invention and liposomal vectors commercially available. This study was carried out using the optimal experimental conditions for each tested method.

Figure 2:
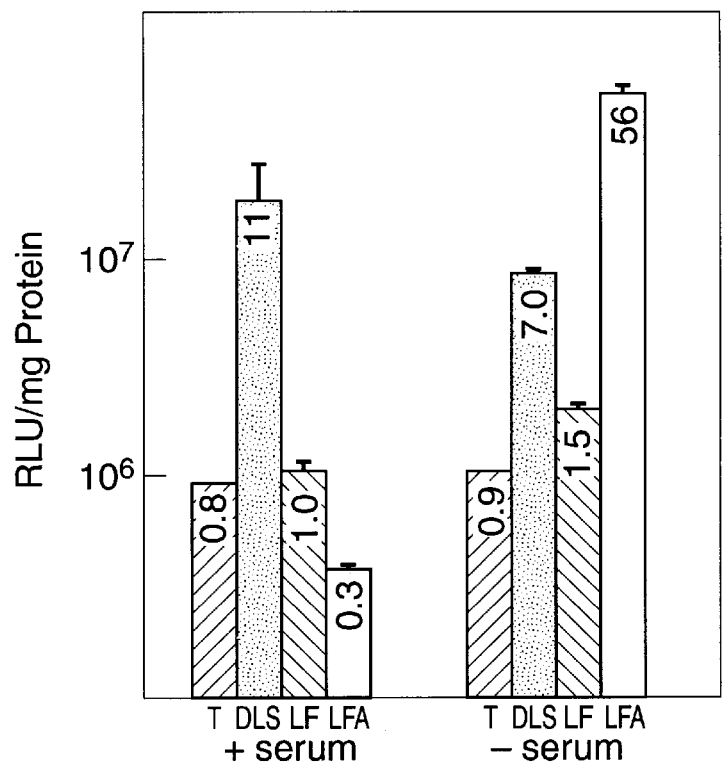
FIG. 2: Comparative study of the transfection efficiency of DLS and other liposomal delivery systems. Luciferase activity was assayed in HeLa cells transfected with pRSV luc plasmid in presence or in absence of serum (15%) T: DOGS or Transfectam (Promega, Madison, Wis.); LF: Lipofectin (Gibco BRL, Gaithersburg, Md.); LFA: Lipofectamine (Gibco BRL).

In serum-containing cell culture medium transduction efficiency in HeLa cells treated with the liposomal system in accordance with this invention appears to be 11-fold, 10-fold and 37-fold higher than that of DOGS or Transfectam (Promega, Madison, Wis.), Lipofectin and Lipofectamine (GIBCO BRL, Gaithersburg). (FIG. 2)

In serum-free medium which is not corresponding to a biological environment, transduction efficiency using DOGS/DOPE liposomes appears equivalent to that determined when cells are incubated in serum-containing medium. In contract, use of Lipofectamine in serum-free conditions make possible a high transfection efficiency. The dramatic decrease in transduction efficiency (186-fold) using Lipofectamine in a medium containing Fetal Bovine Serum (10%) underlines the high instability of DNA when exposed to nucleases, and the need for complete DNA protection toward enzymatic attack in a biological environment. DOGS/DOPE liposomes prepared in accordance with this invention exhibit an effective cell delivery and an efficient DNA protection during transport.

Figure 3:
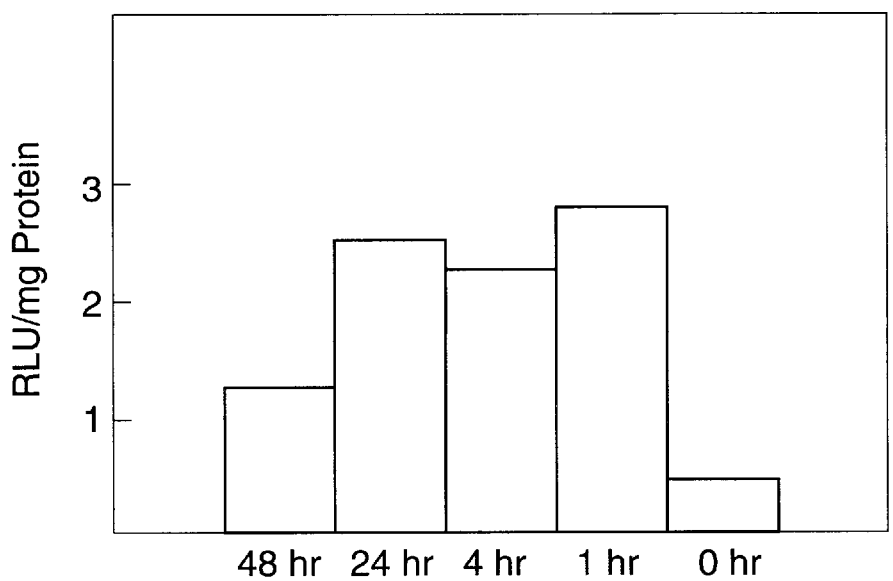
FIG. 3: Effect of preincubation in culture medium on DLS transfection efficiency in HeLa cells. Luciferase activity was ascertained following transfection of liposomal DNA preincubated in serum containing medium (15%).

As illustrated in FIG. 3, preincubation of liposomal DNA in serum containing medium up to 48 hours does not decrease transfection efficiency. In contrast, a significant increase was observed, suggesting the presence in the serum of a factor helping gene transfer.

Figure 4:
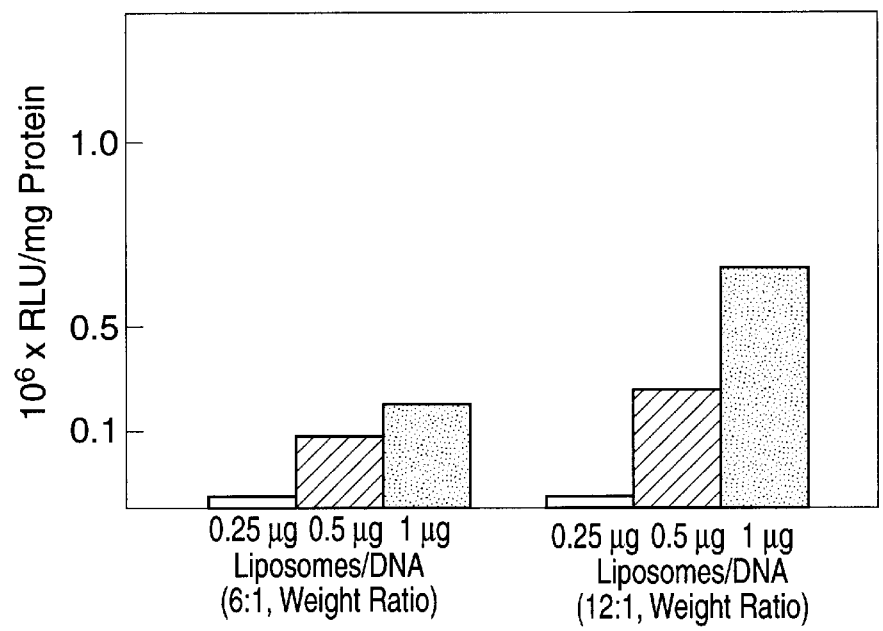
FIG. 4: Transfection efficiency in HeLa cells with liposomal DNA. Luciferase activity was determined.

FIG. 4 shows optimal transfection efficiency by using a 12:1 liposome/DNA weight ratio for the preparation of the liposomal DNA.

Figure 5:
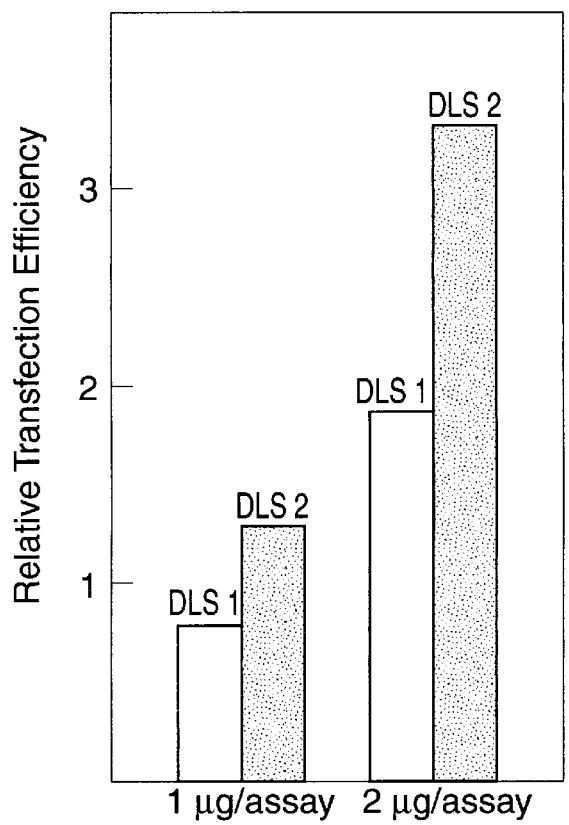
FIG. 5: Relative transfection efficiency of DLS-1 and DLS-2 in HeLa cells using pRSV luc.

As illustrated in FIG. 5, use of plasmid DNA delivered by DLS-2 showed better transduction efficiency in HeLa cells when compared to the DLS-1 delivery. This may be due to increase in DNA protection toward nuclease attack and/or better release from endocytic vesicles when encapsulated in liposomes.

EXAMPLE 5

Preparation of Oligonucleotides containing DOGS/DOPE Liposome Composition

Oligonucleotides may be complexed or encapsulated in DLS-liposomes using the methodological procedure described in examples 2 and 3, respectively. The only modification is that a two-fold higher nucleic acid/liposome ratio may be used for DLS-1 (20 µg/60 µg, weight ratio) at equivalent encapsulation efficiency. This leads to a higher concentration of oligonucleotides in the liposome preparation and consequently a higher efficiency of delivery in terms of quantity of nucleic acids delivered per cells.

EXAMPLE 6

Intracellular Distribution of Nucleic Acid after Delivery with DLS-Liposomes

Nucleic acid cell penetration and its intracellular distribution following delivery using DLS-liposomes were observed using laser-assisted confocal microscopy and FITC-labeled oligodeoxynucleotides (20 mers). The former technique allows for the high resolution of optical sections of suspension cell preparations and can readily specify the intracellular distribution of a fluorescent compound. FIG. 6 presents images of hepatocyte HepG2 cells treated with DLS-1 encapsulated oligodeoxynucleotides for 24 hrs.

Figure 6A:
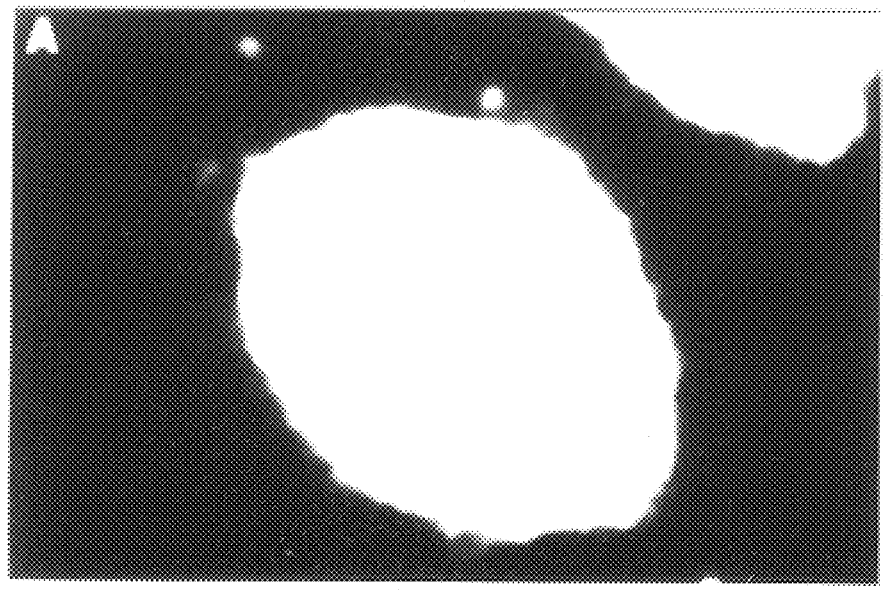
FIG. 6: Intracellular localization of FITC-end labeled oligodeoxynucleotides (20 mers)) in HeLa cells following DLS treatment. Cells were exposed to 2 μM FITC-labeled oligodeoxynucleotides for 24 hr (A, B) and the post-incubated in drug-free medium for 24 hr (C)—Cells were treated with 2 μM free FITC-labeled oligodeoxynucleotides for 24 hr (D). Photographs represent computer-enhanced images from laser-assisted confocal microscopy. Magnification, ×320.
Figure 6B:
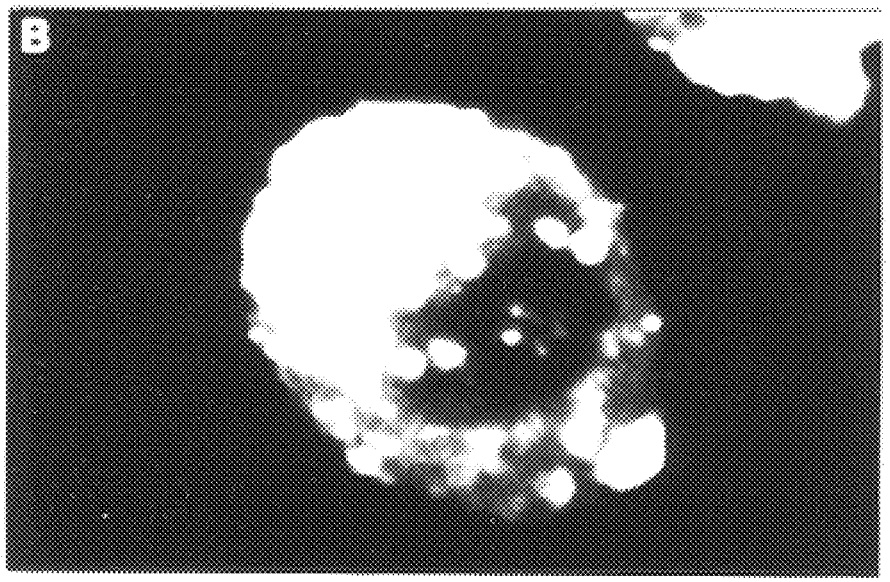
Figure 6C:
Figure 6D:
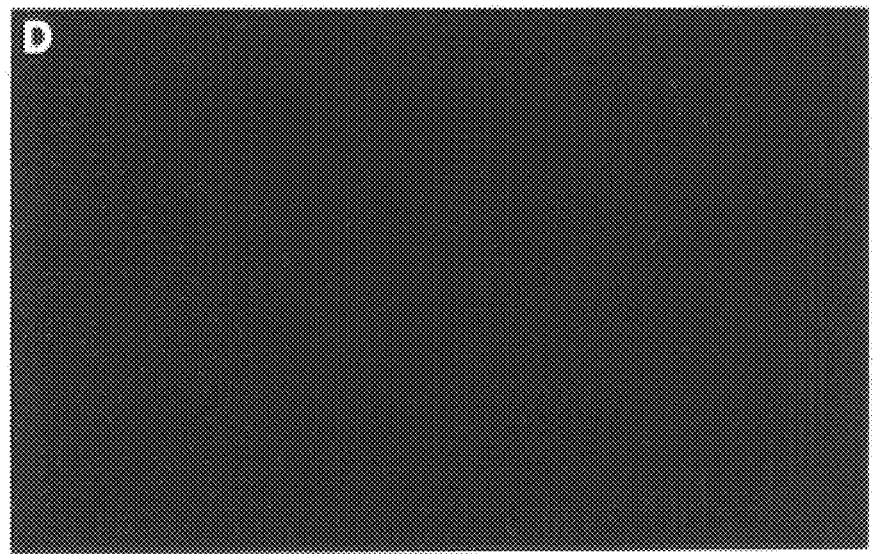

We observed a high penetration of the labeled oligodeoxynucleotides in all intracellular compartments (FIG. 6A). In order to investigate where oligodeoxynucleotides are highly concentrated, we significantly reduce the gain of the laser beam used for confocal microscopy observation of the same cell, and we observed a punctuated intra-cytoplasmic distribution of the oligonucleotides (FIG. 6B). This suggests that DLS transports oligonucleotides into cells via endocytosis and then oligonucleotides quickly escape from endocytic vesicles leading to a release of free oligonucleotides in the cytoplasm. Oligonucleotides are immediately transported from the cytoplasm to the nucleus (FIG. 6C). An extremely weak fluorescence intensity was observed in cells incubated with free labeled oligonucleotides, suggesting poor penetration and/or degradation by nucleases present in the serum-containing culture medium (FIG. 6D).

This observation is of great interest since it shows efficient delivery of nucleic acids to cells, total and immediate escape from endocytic vesicles where active degradation could take place, and nuclear localization after cell treatment. Theoretically, cell delivery of plasmid-DNA via DLS may use the same pathway of cell internalization.

EXAMPLE 7

Preparation of a DOGS/DOPE Containing Liposome Composition with Adenovirus Particles Formation of liposomes make possible anchorage to the membrane bilayer of products which may increase transduction efficiency. Viruses, in general, are inherently excellent gene transfer vectors. Viral capsids or envelopes exhibit specific structure and contain molecules leading to efficient delivery of their genetic content to the infected cells. In order to exploit this property, adenovirus particles (without DNA or denatured by irradiation) have been attached to the liposomal membrane of the liposomes prepared according to the present invention. It is established that adenoviruses enter cells via receptor-mediated endocytosis. A specific fusogenic mechanism makes possible the release of the viral genetic content from the cellular endocytic vesicles after internalization. Use of adenovirus to facilitate gene transfer has been reported (1). Although DLS-liposomes clearly show a significant escape from intracellular vesicles, presence of adenovirus capsids at the liposome surface may enhance transduction efficiency by facilitating intracellular vesicle disruption.

The adenovirus strain used in the present invention is the dl 312 strain received as a gift from T. Shenk (Princeton Univ., Princeton, N.J.). Any adenovirus strain can be used in the present invention. Preparation of adenovirus capsids (no DNA) using cesium chloride gradient method may be performed following adenovirus collection and preparation. Whole adenovirus particles (with DNA) but inactivated by UV irradiation (10 J.m$^{-2}$ 8-1) may also be used. Hydrophobic binding of adenovirus to the liposomes is carried out by simply mixing the liposome suspension with the adenovirus concentrate. For instance, particles equivalent to $10^8$ PFU (Plating Forming Unit) are added to 12.5 μl of a DLS-liposome-associated DNA preparation corresponding to 1 μg DNA and 12.5 μg lipids. The mixture is slightly homogenized and then incubated at 37 C for 1 hr with gentle shaking. Immediately after incubation adenovirus-DNA liposome preparation is added to cell culture. Transfection procedure is the same as that used for DLS liposomes.

FIG. 7 illustrates that adenovirus associated liposomes greatly enhance transfection efficiency in HeLa cells by a factor 4.5. Transfection efficiency obtained after simultaneous addition in cell culture medium of liposomal DNA and adenovirus particles at equivalent concentration was significantly lower (2.7-fold). This demonstrates the specific additional effect of the adenovirus particles attachment to the liposomes on gene expression and particularly on the plasmid DNA escape from endocytic vesicles.

EXAMPLE 8

Electron Microscopy Study

DLS-liposomes and Transfectam TM (Promega, Wis.) reagent (DOGS) samples were submitted to negative staining and Transmission Electron Microscopy (TEM) analysis. The following is a part of the observations independently made by ABI Inc (Columbia, Md.).

DLS-liposomes: "Lipidic particles were observed throughout this preparation and were found in large quantities". "Each different particle appeared to display a heavily stained core region, which was surrounded by many different layers of membranes or envelopes. The particles contained so many different layers of membranes, it was difficult to establish the size of one lipidic particle to the next. Although it was difficult to measure the overall size of the particles, due to their pleomorphic shape and varied number of layers, it appeared the particles ranged from 200 to 3000 nm in diameter. The grid areas showed a high concentration of smaller lipidic particles throughout the background of the sample".

Transfectam reagent (DOGS): "Possible lipidic particles were found in this sample, in small quantities. The particles found in this sample were very different from those observed in the previous sample. The lipidic particles observed appeared to be either in the process of breaking down or they had never properly been formed. Large areas of lipid-like material were observed, however, they did not display any ultrastructural detail, such as different layers of membranes. The only similarity between this sample and the previous sample was that the lipidic particles were heavily stained. Very little debris was found in the background of the sample."

Thus, TEM analysis demonstrated that DLS-liposomes are formed of bilayer membranes vehicles. This specific ultrastructure differentiate them to Transfectam reagent or other cationic liposomes so far commercialized such as Lipofectin (BRL Co., N.Dak.). These later when complexed with DNA is not constituted of membrane bilayer-containing vesicles but is rather a lipid coating particle that presumably contain nucleic acids. Thus they may not be liposomes in the true sense of the term. DLS-liposomes better efficacy in transferring DNA may be explained by their liposomal structure. Furthermore, we may expect improved pharmacokinetic properties such as increased plasma half life. In addition, the presence of membrane bilayer in DLS-liposomes makes possible the anchorage of antibody to their surface which may result in cell targeting.

EXAMPLE 9

Expression of the mdr-1 Gene in Cultured Murine Bone Marrow Cells

The mdr-1 gene expresses the P-glycoprotein ("P-gp"), a plasma membrane protein involved in the emergence of the Multi-drug Resistance phenotype which may occur after chemotherapy. The mdr-1 gene was used in this example as a marker of gene delivery in order to assess the efficacy of bone marrow transplant of mdr-1 gene transfected bone marrow cells by DLS-liposomes.

In order to assess the efficacy of bone marrow transplantation for "ex vivo" gene therapy, murine bone marrow cells were transfected with this plasmid and the DLS-liposomes and transplanted into Balb-C mice. The proliferation and differentiation of transduced hematopoeitic progenitor cells were detected up to 21 days after transplantation in the spleen and the bone marrow, suggesting that the bone marrow transplant had taken place.

Murine bone marrow cells were harvested and quickly transfected with the pHaMDR GA plasmid encapsulated in DLS-liposomes. Seven different experiments have confirmed that the mdr-1 gene was expressed in bone marrow cells since cells continue to grow under selective pressures (vincristine). In addition, lymphocyte, macrophage and fibroblast populations have been shown to exhibit the MDR phenotype after selection (using the rhodamine drug efflux method).

EXAMPLE 10

In Vivo Administration of DLS-Liposomes into Balb-C Mice

Plasmid vector containing the luciferase gene as a marker gene were delivered by DLS-liposomes in Balb-C mice. Various formulations of liposomes encapsulated plasmid at various DNA/lipid ratios were assayed. In these experiments transgene expression has been assayed in liver, lung and spleen. Luciferase activity was determined by bioluminescence measurement (2–3 mice/point). More than 100 mice have been studied. PCR analysis showed the long lasting expression of the luciferase gene in all tissues tested (lung, liver, heart, spleen, skeletal muscle, blood cells, bone marrow, and ovary) up to at least 2 months post-injection. Only episomal replicating DNA vectors showed positive results.

EXAMPLE 11

Intravenous Administration of DLS-Liposomes Containing Plasmid DNA

Luciferase gene expression was detected in lungs liver and heart after 3, 10, 30 days post-injection of DLS-liposomes containing plasmid DNA at a dose of 50 and 100 ug DNA/mouse. The relative expression in these organs largely depends on the DNA/lipid ratio used. The optimal liposome formulation was determined to be 10 mg DNA/50 mg lipid. The toxicity was very limited for doses lower than 100 ug/mouse. The toxicity in humans is approximately 5 mg DNA/kg.

EXAMPLE 11

Intraperitoneal Administration of DLS-Liposomes Containing DNA

Luciferase gene expression was detected in spleen 3 days post-injection. The dose injected per mouse was 100 ug. No toxicity was detected.

EXAMPLE 12 mdr-1 Gene Expression in Blood Cells After Intravenous Administration in Mice

Intravenous injection of mice with DLS-liposomes containing pHaMDR GA plasmid resulted in expression of the mdr-1 gene in circulating lymphocytes and granulocytes 10–15 days post-injection. Mice were pretreated with 5-FU before administration of DLS-liposomes.

EXAMPLE 13

Inhibition of KS Y-1 Cell Tumorigenicity

The present invention can be used in the therapy of Kaposi's Sarcoma ("KS"). Two KS cell lines, showing tumorigenic properties in vitro and in vivo, have recently been established. One cell line, KS Y-1, was derived from a lesion of an HIV-infected individual. The second cell line, KS N1506, was derived from a lesion of a non-HIV associated immunodepressed individual. High amounts of IL-6, IL-8, and VEGF are produced in these cell lines. Correspondingly, high levels of these cytokines have also been found in the serum of AIDS-KS patients. In this example, antisense oligo(dN) was used as a specific molecular tool to inhibit KS cell production of these factors.

0.1 uM VEGF antisense phosphodiester oligodeoxynucleotides encapsulated in DLS-liposomes completely blocked KS Y-1 cell colony formation in semisolid culture. Lipofectin liposomes required 7–10 fold higher concentration to achieve the same inhibitory effect.

REFERENCES

The hereinbelow list of references provides a complete citation of each of the references cited hereinabove. All of the references mentioned in the present application are incorporated in toto into this application by reference thereto.

1. CRISTIANO R. J., SMITH L., and WOO S. L. *Proc. Natl. Acad. Sci. USA* 90, 2122–2126 (1993)
2. NABEL E. G., PLAUTZ G., and NABEL G. J. *Science* 249, 1285–1288 (1990)
3. FELGNER P. L., GADEK T., HOLM M. et al. *Proc. Natl. Acad. Sci. USA* 84, 7413–7417 (1987)
4. WANG C. and HUANG L. *Proc. Nat. Acad. Sci. USA* 84, 7851–7855 (1987)
5. GAO X. and HUANG L. *Biochem. Biophys. Res. Commun.* 179, 280–285 (1991)
6. ZHU N., LIGITT D., LIU Y., and DEBS R. *Science* 261, 209–211 (1993)
7. SORIANO P., DIJUSTRA J., LEGRAND A. et al. *Proc. Natl. Acad. Sci. USA* 80, 7128–7131 (1983)
8. OSTRO M. J. and CULLIS P. R. *Amer. J. Hosp. Pharm.* 46, 1576–1587 (1989)
9. BEHR J. P., DEMENEIX B., LOEFFLER J. P. and PEREZ-MOTUL J. *Proc. Natl. Acad. Sci. USA* 86, 6982–6986 (1989)
10. BARTHEL F., REMY J. S., LOEFFLER J. P. and BEHR J. P. *DNA Cell Biol.* 12, 6, 553–560 (1993)

I claim:

1. A liposome composition comprising a cationic lipopolyamine and a neutral lipid, wherein the cationic lipopolyamine comprises spermine-5-carboxy-glycinedioctadecylamide.

2. A liposome composition according to claim 1 wherein the neutral lipid comprises dioleylphosphatidyl ethanolamine or phosphatidylethanolamine.

3. A liposome composition of claim 1 wherein the neutral lipid is dioleylphosphatidyl ethanolamine.

4. A liposome composition of claim 1 wherein the neutral lipid is phosphatidyl ethanolamine.

5. A nucleic acid-liposome composition comprising the liposome according to claim 1 and a nucleic acid.

6. A nucleic acid-liposome composition comprising the liposome according to claim 2 and a nucleic acid.

7. A nucleic acid-liposome composition comprising the liposome according to claim 3 and a nucleic acid.

8. A nucleic acid-liposome composition comprising the liposome according to claim 4 and a nucleic acid.

9. A nucleic acid-liposome composition according to claim 5 wherein the nucleic acid comprises an antisense oligonucleotide.

10. A nucleic acid-liposome composition according to claim 5 wherein the nucleic acid comprises a plasmid DNA.

11. A liposome composition according to claim 1 prepared by a method comprising:
   a-mixing a cationic lipopolyamine and a neutral lipid forming a mixture;
   b-evaporating the mixture to dryness, forming a dried lipid film;
   c-rehydrating the dried lipid film forming the liposome.

12. A liposome composition according to claim 11 wherein the method of preparation further comprises: adding a nucleic acid, after rehydrating the dried lipid film.

13. A liposome composition according to claim 11 wherein the method of preparation further comprises: adding a nucleic acid, upon rehydration.

14. A pharmaceutical composition comprising a nucleic acid-liposome composition according to claim 5 and a suitable carrier.

15. A pharmaceutical composition comprising a nucleic acid-liposome composition according to claim 6 and a suitable carrier.

16. A pharmaceutical composition comprising a nucleic acid-liposome composition according to claim 7 and a suitable carrier.

17. A pharmaceutical composition comprising a nucleic acid-liposome composition according to claim 8 and a suitable carrier.

18. A method of introducing a nucleic acid into cells of a subject comprising administrating to the subject an effective amount of a nucleic acid liposome composition according to claim 5.

19. A nucleic acid-liposome composition comprising the nucleic acid-liposome of claim 5 and adenovirus particles.

20. A nucleic acid-liposome composition comprising the nucleic acid-liposome of claim 8 and adenovirus particles.

21. A liposome composition according to claim 12, the method of preparation further comprising the step of:
   mixing the liposome with adenovirus particles.

22. A liposome composition according to claim 13, the method of preparation further comprising the step of:
   mixing the liposome with adenovirus particles prior to the addition of the nucleic acid.

* * * * *